United States Patent [19]

Tanaka et al.

[11] Patent Number: 5,322,947
[45] Date of Patent: Jun. 21, 1994

[54] PROCESS FOR PRODUCING N,N'-BIS(2,2,6,6-TETRAMETHYL-4-PIPERIDYL)ALKANEDIAMINE

[75] Inventors: Shinya Tanaka, Toyonaka; Manji Sasaki, Nishinomiya; Shinichi Yachigo, Toyonaka; Hiroki Yamamoto; Eiiti Yoneyama, both of Niihama, all of Japan

[73] Assignee: Sumitomo Chemical Company, Limited, Osaka, Japan

[21] Appl. No.: 4,667

[22] Filed: Jan. 14, 1993

Related U.S. Application Data

[63] Continuation of Ser. No. 722,299, Jun. 27, 1991, abandoned.

[30] Foreign Application Priority Data

Jun. 29, 1990 [JP] Japan .................................. 2-173138
Mar. 19, 1991 [JP] Japan .................................. 3-054406

[51] Int. Cl.$^5$ .......................................... C07D 401/14
[52] U.S. Cl. .................................................. 546/186
[58] Field of Search .......................................... 546/186

[56] References Cited

U.S. PATENT DOCUMENTS

| | | | |
|---|---|---|---|
| 4,086,204 | 4/1978 | Cassandrini et al. | 524/101 |
| 4,104,248 | 8/1978 | Cantatore | 524/103 |
| 4,331,586 | 5/1982 | Hardy | 525/186 |
| 4,607,104 | 8/1986 | Malz, Jr. et al. | 546/186 |

FOREIGN PATENT DOCUMENTS 0302020 7/1988 European Pat. Off.

OTHER PUBLICATIONS

Condensed Chemical Dictionary 5th Ed. Grant & Hackh's, p. 161 "Crystallization".

*Primary Examiner*—Marianne M. Cintins
*Assistant Examiner*—Catherine S. Kilby Scalzo
*Attorney, Agent, or Firm*—Stevens, Davis, Miller & Mosher

[57] ABSTRACT

Crude N,N'-bis(2,2,6,6-tetramethyl-4-piperidyl)alkanediamine represented by the formula:

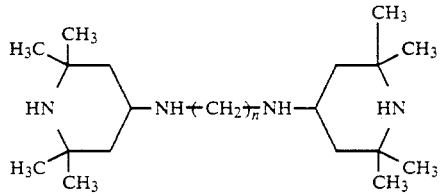

wherein n is an integer of 2 to 10, is purified by crystallization from a ketone solvent of 3 to 9 carbon atoms. The purified product thus obtained has a purity of 98% by weight or more, a 2,2,6,6-tetramethyl-4-piperidone content of 150 ppm or less, and an initial APHA value of 30 or less. The purified product is also inhibited from discoloration with the passage of time.

4 Claims, No Drawings

PROCESS FOR PRODUCING N,N'-BIS(2,2,6,6-TETRAMETHYL-4-PIPERIDYL)ALKANEDIAMINE

This application is a File Wrapper continuation of application Ser. No. 07/722,299, filed Jun. 27, 1991, now abandoned.

The present invention relates to a process for producing a purified N,N'-bis(2,2,6,6-tetramethyl-4-piperidyl)alkanediamine having a high purity and exhibiting a small tendency to discoloration, from a crude product thereof. The N,N'-bis(2,2,6,6-tetramethyl-4-piperidyl)alkanediamine to be purified in the present invention is represented by formula (I):

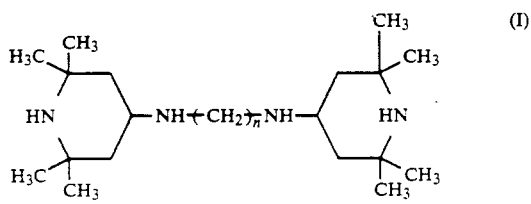

wherein n is an integer of 2–10, and the compound is hereinafter referred to as "piperidine compound".

The piperidine compound represented by formula (I) is useful as an intermediate for light stabilizers etc. used in polymeric substances (see, for example, U.S. Pat. Nos. 4,086,204 and 4,331,586, etc.).

Usually, the piperidine compound of formula (I) is produced by subjecting 2,2,6,6-tetramethyl-4-piperidone and an alkanediamine such as hexamethylene-diamine to hydrogenation under pressure in the presence of a hydrogenation catalyst such as platinum. The resultant crude product is, in general, further subjected to a purification step, and for example, a purification by distillation is known (U.S. Pat. No. 4,104,248 and European Patent Application Publication No. 302,020). Moreover, European Patent Application Publication No. 302,020 suggests also a purification by crystallization.

However, the purification by distillation requires conditions of a high temperature and a high vacuum such as 180°–190° C. and approximately 1 mmHg, and hence requires a special plant for distillation. Accordingly, such a purification cannot be regarded as a preferred process for industrial application. The purification by distillation is also accompanied by decomposition of products during the distillation, and hence it is hard to obtain the piperidine compound being excellent in initial hue. Moreover, it has been clarified that the purified product obtained from such a process has the problems that the product is discolored during storage and a light stabilizer prepared from the purified product is discolored.

On the other hand, a purification by crystallization is suggested in the above-mentioned European Patent Application Publication No. 302,020, but no specific conditions therefor are described. Moreover, in case of employing hydrocarbons such as n-hexane or alcohols such as methanol as a crystallization solvent, the initial hue of the product is slightly improved, but similarly to the process by distillation, there still remain the problems that the resultant piperidine compound is easily discolored during storage and that a light stabilizer prepared from the resultant piperidine compound is also discolored. Further, a low crystallization yield is found in such crystallization method.

The present inventors have made intensive research to overcome these problems, and resultantly have found that the use of a specific crystallization solvent, i.e. a ketone, brings about a successful result. In addition, the inventors have also found that the discoloration of the piperidine compound represented by formula (I) during storage is chiefly caused by one of the starting materials for preparing the same, 2,2,6,6-tetramethyl-4-piperidone, and that the piperidine compound having good initial hue and having a low 2,2,6,6-tetramethyl-4-piperidone content is inhibited from discoloration during storage.

Thus, the present invention provides a process for producing a purified piperidine compound represented by formula (I), which comprises dissolving a crude product of the piperidine compound represented by formula (I) in a ketone having 3 to 9 carbon atoms, and subjecting the resulting solution to a crystallization.

The present invention also provides a purified piperidine compound represented by formula (I) having a purity of 98% by weight or more, a 2,2,6,6-tetramethyl-4-piperidine content of 150 ppm or less, and an initial APHA value of 30 or less.

The APHA referred to herein is an abbreviation of American Public Health Association and the APHA value means a coloration degree according to the standard of the same association, i.e. a coloration degree of a solution which is prepared by dissolving 10 g of a sample in 100 ml of toluene. And the initial APHA value means the APHA value of the piperidine compound immediately after the purification.

The 2,2,6,6-tetramethyl-4-piperidone, the content of which is restricted in the purified piperidine compound of the present invention, is also called triacetonamine, and represented by formula (II):

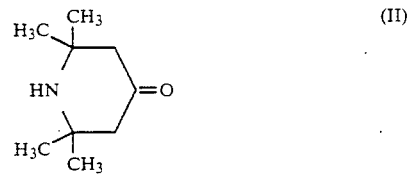

The purified piperidine compound of formula (I) according to the present invention has a purity of 98% by weight or more, a 2,2,6,6-tetramethyl-4-piperidone content of 150 ppm or less, and an initial APHA value of 30 or less. The 2,2,6,6-tetramethyl-4-piperidone content is preferably 120 ppm or less, and the initial APHA value is preferably 20 or less. The purified compound is hardly discolored by oxidation and heat, and hence the compound has no fear of properties changing with time during storage. Furthermore, the light stabilizer derived from the compound is also hardly discolored. Thus, the purified compound can be an intermediate having good qualities for light stabilizers, etc., which qualities have never been achieved by the conventional products.

It has been confirmed that when the 2,2,6,6-tetramethyl-4-piperidone content in the purified piperidine compound of formula (I) is increased over 150 ppm, e.g. to approximately 200 ppm, the piperidine compound clearly becomes easily discolorable. Thus, the removal of 2,2,6,6-tetramethyl-4-piperidone is necessary for producing the piperidine compound of formula (I) which is hardly discolored. However, 2,2,6,6-tetramethyl-4-piperidone is not the only factor for discoloration, and hence it is preferred that other by-products are also removed sufficiently. The initial APHA value of the piperidine compound should be 30 or less as mentioned above, and it is preferable that the piperidine compound has an APHA value of 100 or less even after the passage of time, for example, after holding the compound at 60° C. for 3 months. More preferred is one having an APHA value of 50 or less after such passage of time.

In the piperidine compound represented by formula (I), n is an integer of 2-10, among which compounds, N,N'-bis(2,2,6,6-tetramethyl--4-piperidyl)-hexamethylenediamine, i.e. the compound of formula (I) in which n is 6, is preferably used as an intermediate for light stabilizers.

The piperidine compound of formula (I) can, as stated above, be produced by subjecting 2,2,6,6-tetramethyl-4-piperidone and an alkanediamine to hydrogenation under pressure in the presence of a hydrogenation catalyst such as platinum.

The resultant crude product is subjected to a crystallization in accordance with the process of the present invention. Solvents employed for the crystallization in the present invention are ketones having 3-9 carbon atoms and include, for example, acetone, methyl ethyl ketone, diethyl ketone, methyl isobutyl ketone, diisobutyl ketone, etc. Of these ketones, acetone is particularly preferred. The ketone solvents may contain an alcohol such as methanol, ethanol, isopropanol, or butanol in an amount of 0 to 5% by weight or may contain water in an amount of 0 to 10% by weight.

The amount of the solvent used in the present invention is preferably from about 50 to about 200% by weight based on the weight of the crude piperidine compound, and more preferably from about 70 to about 100% by weight. The crystallization is preferably carried out according to the following procedure:

The above-mentioned solvent is added to the crude piperidine compound obtained by the reaction, the resultant mixture is heated to about 40° C. or higher to dissolve the crude piperidine compound. The heating temperature is generally sufficient up to about 60° C. After the crude piperidine compound is dissolved, the resultant solution is cooled. The cooling can be carried out, for example, by exteriorly contacting the vessel containing the solution with a cooling agent such as water. Crystals begin to precipitate at about 25°-35° C., and the solution is further cooled to about 0°-10° C. The precipitated crystals are separated by, for example, filtration, washed, and then dried to obtain the objective purified piperidine compound.

According to the present invention, a purified N,N'-bis(2,2,6,6-tetramethyl-4-piperidyl)alkanediamine having a high quality and inhibited from discoloration can efficiently be produced by a commercially advantageous crystallization method. The purified product has a low content of 2,2,6,6-tetramethyl-4-piperidone which is the main factor for the discoloration, and also has a desired initial hue without discoloration. Thus, the purified product is excellent in its quality.

Next, the present invention will be explained in more detail with reference to the following examples, which is only illustrative but not limitative to the scope of the present invention. In the examples, percentages and parts are by weight unless otherwise specified.

Reference Example

Synthesis of crude N,N'-bis(2,2,6,6-tetramethyl-4-piperidyl)hexamethylenediamine.

After 1,047 parts of 2,2,6,6-tetramethyl-4-piperidone, 373 parts of hexamethylenediamine, 2,260 parts of methanol and 5.5 parts of 5% platinum-on-carbon catalyst were charged into an autoclave, the temperature of the mixture was gradually elevated from 30° C. and the mixture was subjected to hydrogenation at a hydrogen pressure of 5 kg/cm$^2$ while the temperature was kept at 60°-70° C. It took 8 hours to complete the hydrogenation. The resultant mixture was filtered at about 50°-60° C. to remove the catalyst therefrom, and then the resultant filtrate was subjected to distillation to remove the solvent and the water formed as by-product during the reaction, thereby obtaining 1,325 parts of crude N,N'-bis (2,2,6,6-tetramethyl-4-piperidyl)hexamethylenediamine having a purity of 92.9%, a 2,2,6,6-tetramethyl-4-piperidone content of 0.8%, and an APHA value of 400.

Example of the Invention

To 100 parts of the crude N,N'-bis(2,2,6,6-tetramethyl-4-piperidyl)hexamethylenediamine produced in the Reference Example was added 80 parts of acetone, and the resultant mixture was heated to a temperature close to the boiling point of acetone to dissolve the crude N,N'-bis(2,2,6,6-tetramethyl-4-piperidyl)hexamethylenediamine, after which the resultant solution was cooled by applying cooling water around the vessel in which the solution was contained. Crystals began to precipitate at 29° C. Then the cooling was continued until the temperature reached 5°-10° C. The crystals formed were separated by filtration, washed with acetone, and then dried to obtain 79.6 parts of purified N,N'-bis(2,2,6,6-tetramethyl-4-piperidyl)hexamethylenediamine having a purity of 99.5% and an APHA value of 10.

The purified product was allowed to stand in a thermostat at 60° C. for 3 months to effect a heat-aging test. After the test, the APHA value was 20.

Comparative Example 1

100 parts of the crude N,N'-bis(2,2,6,6-tetramethyl-4-piperidyl) hexamethylenediamine produced in the Reference Example was subjected to simple distillation under the conditions of 200° C. and 0.2 Torr to obtain 82.7 parts of purified N,N'-bis(2,2,6,6-tetramethyl-4-piperidyl)hexamethylenediamine having a purity of 99.7% and APHA value of 100.

The same heat-aging test as in the Example was conducted on the purified product. The results obtained are shown in Table 1.

Comparative Example 2

To 100 parts of the crude N,N'-bis(2,2,6,6-tetramethyl-4-piperidyl) hexamethylenediamine produced in the Reference Example was added 80 parts of acetonitrile, and the resultant mixture was heated up to 60° C. to dissolve the crude N,N'-bis(2,2,6,6-tetramethyl-4-piperidyl) hexamethylenediamine, after which the resultant solution was cooled by applying water around the vessel in which the solution was contained. Crystallization occurred at 25° C. Then the cooling was continued until the temperature reached 5°-10° C. The crystals formed were separated by filtration, washed with acetonitrile, and then dried to obtain 76.3 parts of purified N,N'-bis(2,2,6,6-tetramethyl-4-piperidyl)-hexamethylenediamine having a purity of 99.9%, and an APHA value of 20.

The same heat-aging test as in the Example was conducted on the purified product. The results obtained are shown in Table 1.

Comparative Examples 3-6

Purification was conducted by repeating the same procedure as in Comparative Example 2, except that the solvent for crystallization in Comparative Example 2 was replaced with one of the solvents shown in Table 1.

The same heat-aging test as in the Example was conducted on the purified products. The results obtained are shown in Table 1.

Comparative Example 7

To the purified N,N'-bis(2,2,6,6-tetramethyl-4-piperidyl)hexamethylenediamine produced in the Example was added the starting 2,2,6,6-tetramethyl-4-piperidone in such an amount that the total content thereof was 200 ppm, and then the resultant mixture was subjected to the same heat-aging test as in the Example. The results obtained are shown in Table 1.

Comparative Example 8

To the purified N,N'-bis(2,2,6,6-tetramethyl-4-piperidyl)hexamethylenediamine produced in the Example was added the starting 2,2,6,6-tetramethyl-4-piperidone in such an amount that the total content thereof was 1000 ppm, and then the resultant mixture was subjected to the same heat-aging test as in the Example. The results obtained are shown in Table 1.

What is claimed is:

1. A process for producing a purified N,N'-bis(2,2,6,6-tetramethyl-4-piperidyl) alkanediamine represented by the formula:

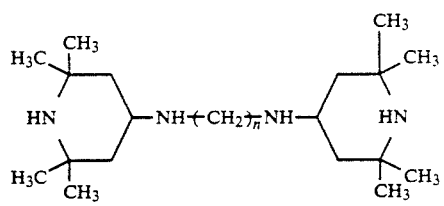

wherein n is an integer of 2 to 10, which process comprises dissolving a crude N,N'-bis(2,2,6,6-tetramethyl-4-piperidyl)alkanediamine represented by the above formula in acetone, and subjecting the resulting solution to a crystallization.

2. The process according to claim 1, wherein the crude N,N'-bis(2,2,6,6-tetramethyl-4-piperidyl)alkanediamine is produced by hydrogenation reaction of 2,2,6,6-tetramethyl-4-piperidone and an alkanediamine.

3. The process according to claim 1, wherein the acetone is used in an amount of from about 50% to about 200% by weight based on the weight of the crude N,N'-bis(2,2,6,6-tetramethyl-4-piperidyl)alkanediamine.

4. The process according to claim 1, wherein the crude N,N'-bis(2,2,6,6-tetramethyl-4-piperidyl)alkanediamine is dissolved in the acetone at a temperature of from about 40° C. to about 60° C., and the resulting solution is cooled to a temperature of from about 0° C. to about 10° C. to crystallize the purified N,N'-bis(2,2,6,6-tetramethyl-4-piperidyl)alkanediamine.

TABLE 1

| | | Method of purification | Solvent for crystallization | Recovery (%) | Purity of products (%) | TAA* (ppm) | Initial APHA | APHA after aging test |
|---|---|---|---|---|---|---|---|---|
| Example | | Crystallization | Acetone | 85.3 | 99.5 | 100 | 10 | 20 |
| Comparative Examples | 1 | Distillation | — | 88.8 | 99.7 | 100 | 100 | >1000 |
| | 2 | Crystallization | Acetonitrile | 82.0 | 99.9 | 500 | 20 | 500 |
| | 3 | Crystallization | n-Hexane | 80.6 | 99.1 | 200 | 50 | 200 |
| | 4 | Crystallization | Toluene | 23.4 | 96.8 | 100 | 50 | 120 |
| | 5 | Crystallization | Methanol | 35.3 | 97.5 | 100 | 30 | 100 |
| | 6 | Crystallization | Water | 99.9 | 98.0 | 500 | 50 | >1000 |
| | 7 | Crystallization | (Acetone) | — | 99.5 | 200 | 10 | 200 |
| | 8 | Crystallization | (Acetone) | — | 99.4 | 1000 | 10 | >1000 |

*TAA: 2,2,6,6-Tetramethyl-4-piperidone

* * * * *